US00PP35842P2

(12) United States Plant Patent
Van Dijk

(10) Patent No.: US PP35,842 P2
(45) Date of Patent: May 28, 2024

(54) ***ANTHURIUM* PLANT NAMED 'AN2656036'**

(50) Latin Name: ***Anthurium andraeanum* L.**
Varietal Denomination: AN2656036

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,520

(22) Filed: Sep. 21, 2023

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./365
See application file for complete search history.

*Primary Examiner* — Susan McCormick Ewoldt
*Assistant Examiner* — Zachariah Allan Kay
(74) *Attorney, Agent, or Firm* — Jondle & Associates, P.C.

(57) ABSTRACT

A new *Anthurium* plant named 'AN2656036' particularly distinguished by having strongly blistered, strongly glossy, pink with green lobes and red tips, oblong-cordate and durable spathes that retain the original color for a very long period of time, weakly glossy, dark green and elliptical-cordate, durable leaves, pink spadices with dark yellowish-brown tips, early and rich flowering continuously throughout the year, and a plant height of 80.0 cm to 90.0 cm is disclosed.

3 Drawing Sheets

Genus and species: *Anthurium andraeanum* L.
Variety denomination: 'AN2656036'.

BACKGROUND OF THE NEW PLANT

The present invention comprises a new and distinct variety of *Anthurium*, botanically known as *Anthurium andraeanum* L., and hereinafter referred to by the variety name 'AN2656036'. The new *Anthurium* plant is a product of a planned breeding program conducted by the inventor in Bleiswijk, the Netherlands. The objective of this breeding program was to create a new cut flower plant with a height of 80.0 cm to 90.0 cm having strongly blistered, strongly glossy, pink with green lobes and red tips, oblong-cordate, durable spathes.

The new variety originated from a cross-pollination made in December 2010 in Bleiswijk, the Netherlands. The female parent was a green *Anthurium* pot plant designated '06-015447-0006' (unpatented), and the male parent was a green *Anthurium* pot plant designated '07-016653-0003' (unpatented).

A single plant was selected from the progeny of the stated cross in February 2013. Asexual reproduction of the new variety by tissue culture in 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 23, 2022 (Application no. 2022/2651), by Applicant who obtained the subject matter disclosed directly from the inventor. 'AN2656036' has not been made publicly available or sold anywhere in the world prior to the effective filing date of this application with the exception of sales or disclosures made one year or less before the effective filing date of this claimed invention by Applicant who obtained 'AN2656036' directly from the inventor.

SUMMARY OF THE INVENTION

The following are the most outstanding and distinguishing characteristics of this new variety when grown under normal horticultural practices in Bleiswijk, the Netherlands:

1) Strongly blistered, strongly glossy, pink with green lobes and red tips, oblong-cordate spathes;
2) Pink spadices with dark yellowish-brown tips;
3) Weakly glossy, dark green, elliptical-cordate leaves; and
4) Spathes: relative position of lobes is incurved, but not touching.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 60-week-old plant grown in a greenhouse in Bleiswijk, the Netherlands, in May 2023. Colors in the photographs may differ from the color values cited in the detailed botanical description, which accurately describes the actual colors of the new variety.

DESCRIPTION OF THE NEW VARIETY

Figure 1:
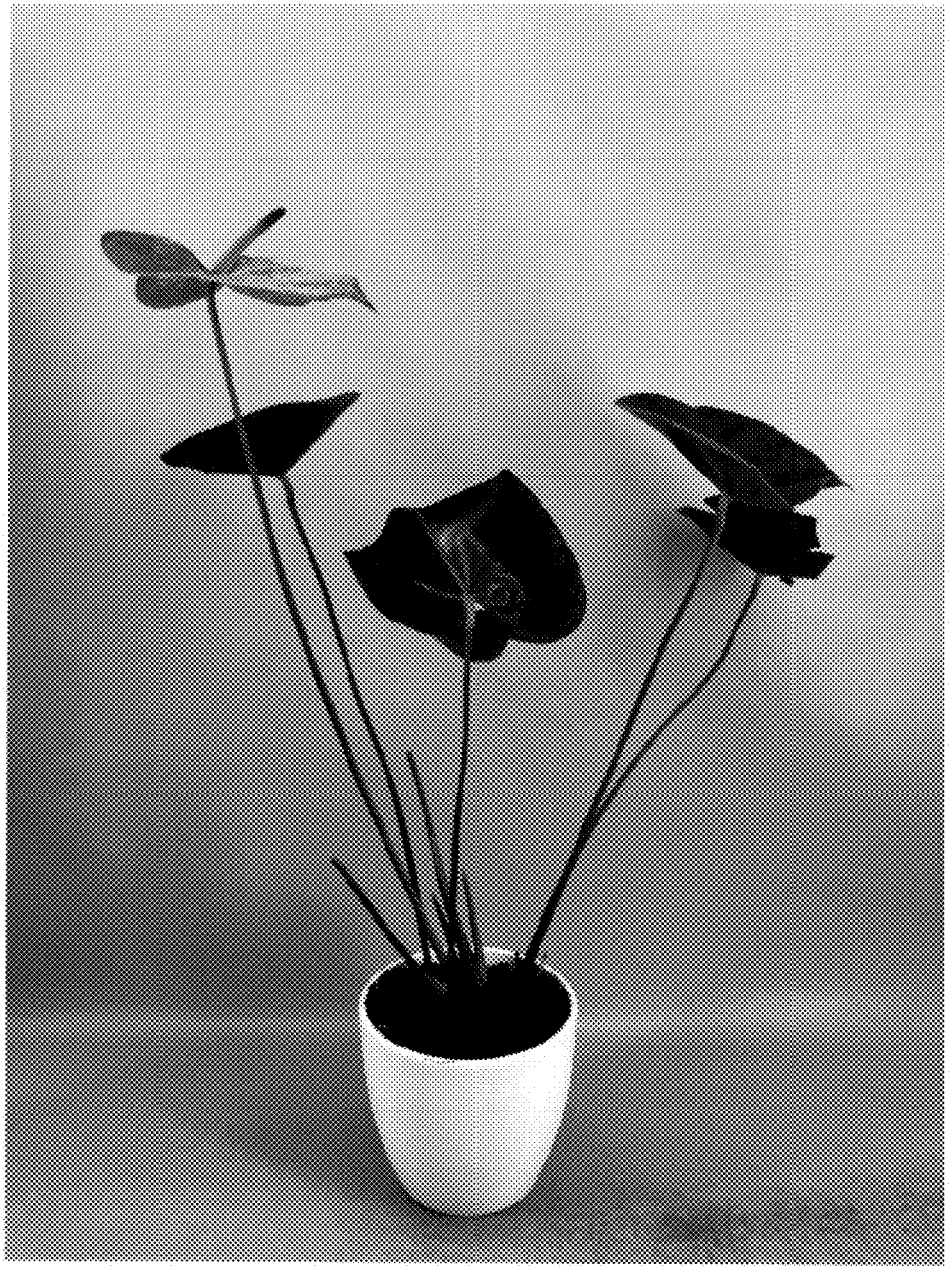
FIG. 1 shows the overall plant habit, including blooms and foliage.
Figure 2:
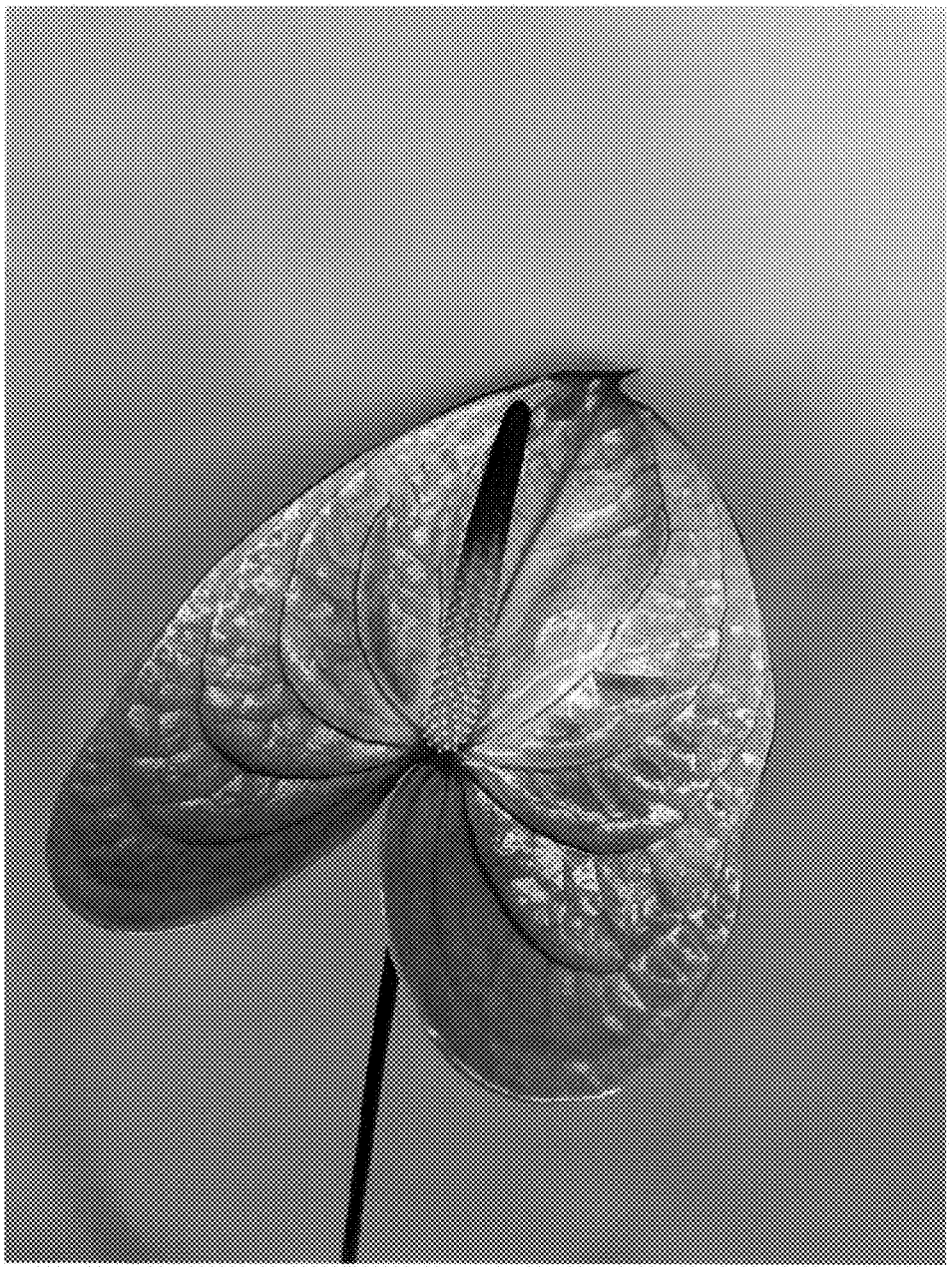
FIG. 2 shows a close-up of the mature spathe.
Figure 3:
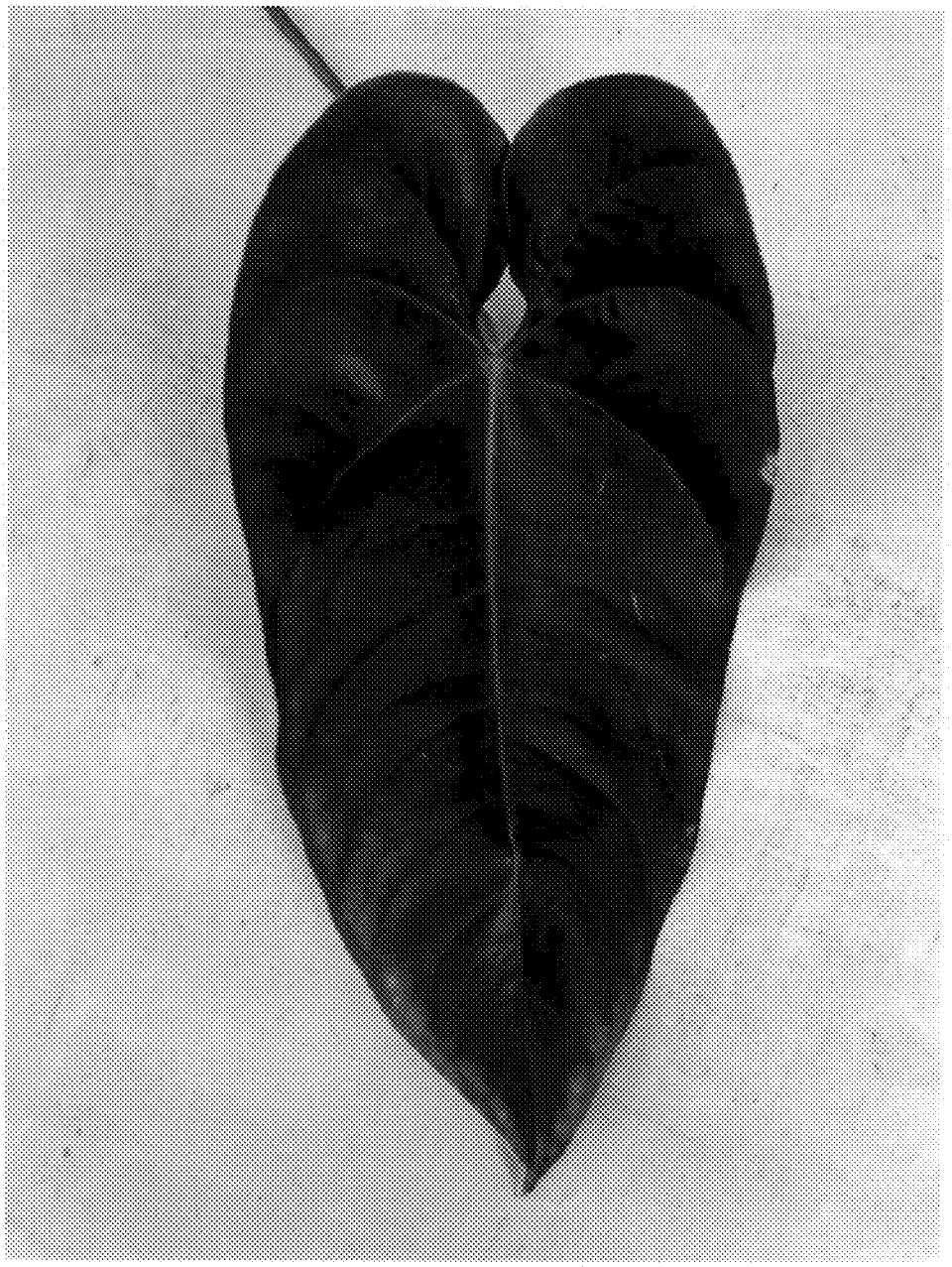
FIG. 3 shows a close-up of the upper leaf blade surface.

The following detailed description sets forth the distinctive characteristics of 'AN2656036'. The data which define these characteristics were collected from asexual reproductions carried out in Bleiswijk, the Netherlands. The plant history was taken on 60-week-old plants which were planted from tissue culture in 17-centimeter (diameter) pots and grown in a glass greenhouse between 19° C. and 24° C. Observations were made in May 2023. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2656036'.

Parentage:

*Female parent*.—*Anthurium* plant '06-015447-0006' (unpatented).

*Male parent*.—*Anthurium* plant '07-016653-0003' (unpatented).

Plant:

*Propagation*.—Tissue culture.

*Root description*.—Fleshy-creamy (RHS 160D) colored roots and small, hairy lateral roots having small, light greenish-yellow (RHS 2D) colored root tips.

*Time to produce a flowering plant*.—55 to 66 weeks after planting in a 17-cm (diameter) pot.

*Growth habit*.—Upright.

*Height* (*measured from soil, including inflorescence*).—80.0 cm to 90.0 cm.

*Width* (*measured from leaf tips*).—55.0 cm to 65.0 cm.

Leaves:

*Immature leaves*.—Length: 27.0 cm to 30.0 cm. Width: 14.0 cm to 16.0 cm. Color: Upper surface: RHS 146A. Lower surface: RHS 146B. Texture (both upper and lower surfaces): Leathery, soft, thin, and strongly glossy.

*Mature leaves*.—Length (fully expanded): 30.0 cm to 33.0 cm. Width: 17.0 cm to 19.0 cm. Shape: Elliptical cordate. Apex: Cuspidate. Base: Cordate. Leaf blade angle with the petiole: Between 120 degrees and 140 degrees. Leaf margin: Entire. Color: Upper surface: RHS 147A. Lower surface: RHS 146A. Texture (both upper and lower surfaces): Leathery, thick, smooth, and weakly glossy. Venation: Pinnate veining; the mid-vein and primary veins (the veins which radiate out from junction of petiole and leaf) protrude at the underside of the leaf blade. Venation color: Upper surface: RHS 144A. Lower surface: RHS 144B.

*Lobes*.—Present. Arrangement: Leaf blade has two lobes extending past the petiole. The lobes are slightly overlapping. Length of lobes of mature leaf blades: 7.0 cm to 8.0 cm. Width of lobes of mature leaf blades: 7.5 cm to 8.5 cm. Distance from petiole/leaf junction to highest point on lobes of mature leaf blades: 6.0 cm to 8.0 cm.

*Petiole*.—Cross-section: Round. Diameter: 0.5 cm to 0.6 cm. Length: 53.0 cm to 58.0 cm for a mature leaf size. Color: Mature leaf: RHS 144A on the front side. Immature leaf: RHS 144B. Cataphyll color surrounding the petiole: Outside: RHS 144A. Inside: RHS 145C.

*Geniculum*.—Length: 2.5 cm to 3.0 cm. Width: 0.6 cm to 0.7 cm. Color: RHS 144B.

Inflorescence:

*Arrangement*.—Single.

*Flowering habit* (*length of flowering season*).—Continuous.

*Number of inflorescences per plant*.—5 to 7 flowers in a period of one year.

*Fragrance*.—Absent.

*Longevity of inflorescence on plant*.—40 to 45 days.

Spathe:

*Buds*.—The spathe is tightly rolled around the spadix and extrudes from the peduncle sheath.

*Arrangement*.—Spathe angle with the peduncle is between 150 degrees and 160 degrees; the spathe stands on a wiry peduncle about 10.0 cm to 20.0 cm above the foliage.

*Shape*.—Oblong-cordate.

*Apex*.—Abruptly acuminate.

*Base*.—Cordate.

*Texture*.—Strongly blistered and strongly glossy.

*Margin*.—Undulated.

*Size*.—Length: 20.0 cm to 22.0 cm. Width: 17.0 cm to 19.0 cm.

*Lobes*.—Present. Arrangement: The spathe has two lobes extending past the peduncle. The lobes are incurved, but not touching. Length: 7.0 cm to 8.0 cm. Width: 8.5 cm to 9.5 cm.

*Color*.—Just fully open: Upper surface: Pink (RHS 180D) with green lobes (RHS 144A) and red tips (RHS N445A). Lower surface: Green (RHS 144B); lighter green (RHS 145C) and red tips (RHS 181B) toward the tips.

Peduncle:

*Shape*.—Erect.

*Cross-section*.—Round.

*Length*.—63.0 cm to 68.0 cm.

*Diameter*.—0.6 cm to 0.7 cm.

*Color*.—RHS 144A.

Flowering time:

*General*.—One small, rooted, untreated tissue culture plant of 4.0 cm tall will flower for the first time, depending on the season, after 30 to 35 weeks.

Spadix:

*Size*.—Length: 6.5 cm to 7.5 cm (depending on flower size). Width (at apex): 0.7 cm to 0.8 cm. Width (at base): 0.9 cm to 1.1 cm.

*Shape*.—Columnar.

*Angle of spadix tip with peduncle*.—110 degrees to 130 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: Reddish-orange (RHS 169A) toward the tips and dark yellowish-brown tips (RHS N199B). Mature: Pink (RHS 5 1B). Ages to: Green (RHS 148A).

Flowers:

*Quantity per spadix*.—380 to 430.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 158C.

Reproductive organs:

*Stamens*.—Not visible.

*Pollen amount*.—Absent.

*Pistil*.—Quantity: 438 to 430. Length: Less than 0.01 cm. Color: RHS 158C.

*Style*.—Not observed to date.

*Stigma*.—Shape: Ovoid. Diameter: Less than 0.01 cm. Color: RHS 158C.

*Ovary*.—Rarely visible.

*Ovary color*.—Not measured.

Fruit and seed set: Fruit and seed production has not been observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2656036' differs from the female parent plant '06-015447-0006' (unpatented) in that 'AN2656036' has oblong-cordate spathes that are pink on the upper side, basal part shortly before dehiscence of anthers is pink, and distal part shortly before dehiscence of anthers is dark yellowish-brown, whereas '06-015447-0006' has orbicular-cordate spathes that are green on the upper side, basal part shortly before dehiscence of anthers is white, and distal part shortly before dehiscence of anthers is green.

'AN2656036' differs from the male parent plant '07-016653-0003' (unpatented) in that 'AN2656036' has very large spathes, dark yellowish-brown distal part shortly before dehiscence of anthers, and elliptical-cordate leaves, whereas '07-016653-0003' has medium spathes, red distal part shortly before dehiscence of anthers, and narrowly long cordate leaves.

'AN2656036' differs from the similar commercial variety 'ANTOSNA' (unpatented) in that 'AN2656036' has elliptical-cordate leaves that are slightly overlapping, and the upper side of the spathes are pink, whereas 'ANTOSNA' has ovate-cordate leaves that are adpressed, and the upper side of the spathes are green.

'AN2656036' differs from the similar commercial variety 'ANTHIRFAP' (unpatented) in that 'AN2656036' has spathes that are pink on the upper side, basal part shortly before dehiscence of anthers is pink, elliptical-cordate leaves, and green petiole, whereas 'ANTHIRFAP' has spathes that are light green on the upper side, basal part shortly before dehiscence of anthers is dark red, ovate-cordate leaves, and brown petiole.

I claim:

1. A new and distinct variety of *Anthurium* plant named 'AN2656036', substantially as illustrated and described herein.

* * * * *